United States Patent [19]

Kállay et al.

[11] 4,150,034
[45] Apr. 17, 1979

[54] PROCESS FOR THE PREPARATION OF SUBSTITUTED-PHENYL-N-ALKYL-CARBAMATES

[75] Inventors: Tamás U. Kállay; Gábor Szabó; Géza Tóth; Kálman Harsányi, all of Budapest, Hungary

[73] Assignee: Chinoin Gyogyszer es Vegyeszeti Termekek Gyara Rt., Budapest, Hungary

[21] Appl. No.: 823,504

[22] Filed: Aug. 10, 1977

Related U.S. Application Data

[63] Continuation of Ser. No. 463,031, Apr. 22, 1974, abandoned.

[30] Foreign Application Priority Data

Apr. 24, 1973 [HU] Hungary .................. CI 1367

[51] Int. Cl.² .......................................... C07D 339/02
[52] U.S. Cl. ............................. 260/327 M; 260/340.7; 560/132; 560/135
[58] Field of Search .................. 260/327 M, 340.7; 560/132, 135

[56] References Cited

U.S. PATENT DOCUMENTS 3,781,301  12/1973  Nikles et al. .................. 260/327 U
3,910,991  10/1975  Nikles et al. .................. 566/132

FOREIGN PATENT DOCUMENTS 1166180  3/1964  Fed. Rep. of Germany ........... 560/132

OTHER PUBLICATIONS

Bodanszky, Nature, vol. 175, p. 685, 1955.
The Peptides I, pp. 97 to 98 (1965).

*Primary Examiner*—John D. Randolph
*Attorney, Agent, or Firm*—Karl F. Ross

[57] ABSTRACT

A process for the preparation of a substituted-phenyl-N-alkyl-carbamate of the formula

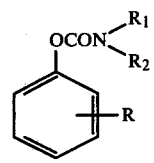

wherein
$R^1$ and $R^2$ form part of a carbamoyloxy group and are identical or different and each is hydrogen or lower alkyl,
R is halogen, formyl group or a group of the formula

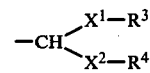

in ortho or meta-position to the carbamoyloxy group, wherein $X^1$ and $X^2$ are identical or different and each is oxygen or sulphur and
$R^3$ and $R^4$ are identical or different and each is alkyl, alkenyl or alkynyl or together form a 5-membered saturated or unsaturated heterocycle in which $X^1$ and $X^2$ are heteroatoms, said process comprising reacting a compound of the formula

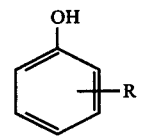

in the presence of a base with a compound of the formula

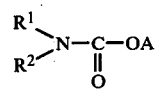

wherein A is phenyl substituted with two or more electron withdrawing groups.

3 Claims, No Drawings

PROCESS FOR THE PREPARATION OF SUBSTITUTED-PHENYL-N-ALKYL-CARBAMATES

This is a continuation of application Ser. No. 463,031, filed Apr. 22, 1974, now abandoned.

The present invention is directed to a process for the preparation of the compounds of the formula I

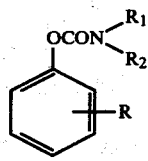

wherein
$R^1$ and $R^2$ are identical or different and each is a hydrogen atom or a lower alkyl group,
R is a halogen atom, aldehyde group or a group of the formula

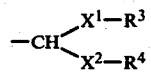

in the ortho or meta-position to the carbamoyloxy group, wherein $X^1$ and $X^2$ are identical or different and each is oxygen or sulphur and
$R^3$ and $R^4$ are identical or different and each is alkyl, alkenyl or alkynyl or together with the whole residue R may for a 5-membered saturated or unsaturated heterocycle, which contains $X^1$ and $X^2$ as heteroatoms)
which comprises reacting a compound of the formula II

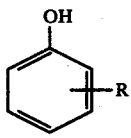

wherein R is defined above, in the presence of a base with a compound of the formula III

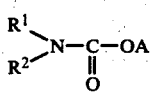

wherein $R^1$ and $R^2$ are defined above and A is a phenyl group, substituted with two or more electron withdrawing groups, preferably A is a pentachlorophenyl-group.

The compounds defined above possess valuable insecticidal and acaricidal effect. Especially valuable representative of the above compound group is the N-methylcarbamic acid-2-(1,3-dioxolane-2-yl)-phenyl-ester. This compound possesses a strong action against insects, houseflies, aphids and e.g. against the Colorado beetle. Compounds of the formula I, wherein $R^1$ is hydrogen, $R^2$ is lower alkyl, e.g. methyl group, and R is a dioxolanyl, oxathiolanyl or dithiolanyl group in the ortho position and, may be used against insects (Hungarian Patent Specification No. 153 303).

Carbamates according to the formula I may be prepared in the presence of a base as a catalyst using alkyl isocyanates in an addition reaction in one step (J. Org. Chem. 28, 658 (1963); Helv. Chim. A. 48, 2005 (1965)); Hungarian Patent Specification No. 153 303).

The preparation of N-substituted-carbamic acid-esters may be carried out in a substitution reaction—by reacting with phosgene—as well; this reaction consists of two steps, the appropriate chloroformiates are formed, which are reacted with a suitable amine (Meth. der Org. Chem. 8, 101 (1952); Chem. Pharm. Bull. 15, 2015 (1967)).

The N,N-disubstituted-carbamic acid-esters of the formula I may be prepared by a one step substitution reaction by using N,N-disubstituted-carbamic acid chlorides.

In the recent literature the preparation of the so-called active carbamic acid-esters-alkyl-urethanes used mainly in the chemistry of peptides, is described. The application thereof as an acylating agent is also mentioned (French Patent Specification No. 879,920; M. Bodanszky; Nature 175, 685 (1955)).

It is known that instead of alkyl-carbamic acid-esters phenyl esters and phenyl urethanes may be more advantageously used, as the activity thereof may be considerably improved by introducing electron withdrawing substituents into the aromatic ring. Particularly halogeno, carbamoyl and nitro substituents are used. (The Peptides I. 98 (1965); Helv. Chim. A. 46, 160 (1963)).

It has been found that the compound of the formula I may be prepared in a new way by means of a one-step substitution reaction by the use of the above mentioned active carbamic acid phenyl-esters; thus pure and homogeneous products are obtained. The compounds of the formula III, i.e. active carbamic acid phenyl-esters are used as acylating agents, wherein $R^1$ and $R^2$ are identical or different and each is a hydrogen atom or a lower alkyl group or a containing 1–4 carbon atoms, A is a phenyl group, substituted with one or more electron withdrawing groups, preferably A is a pentachloro-phenyl group.

The reaction is preferably carried out in a solvent in the presence of a base used in a small molar excess, calculated on the active carbamic acid phenyl-ester.

As the base, inorganic bases, tertiary amines, preferably triethylamine or pyridine may be used.

The reaction is preferably carried out in an organic solvent, in which two of the starting materials (included the base) are dissolved and the formed compound is insoluble or is soluble to such an extent that after precipitating with hexane or after fractionated crystallization no other component precipitates as a contamination.

Aromatic hydrocarbons (e.g. toluene), lower ketones or esters (e.g. acetone, ethyl acetate), ethers (e.g. dioxane) or chlorinated solvents (e.g. chloroform) are preferably used. When using an inorganic base, the purification of the reaction product may be carried out—if necessary—by aqueous suspension thereof.

The compounds of the formula III, the active N-substituted carbamic acid esters may be prepared according to the methods described in the literature for the preparation of phenyl or thiophenyl esters (Liebigs Ann. Chem. 562, 219, 207 (1949); J. Org. Chem. 28, 658 (1963)).

The starting material of the formula II is prepared by acetalzation or mercaptalization of the suitable aromatic aldehydes.

Further details of the present invention are described in the Examples.

EXAMPLE 1

6.75 g (0.0405 moles) of 2-(1,3-dioxolan-2-yl)-phenol are dissolved in 50 ml of anhydrous toluene and 13 g (0.04 moles) of N-methyl-carbamic acid-pentachlorophenylester are added to the mixture with stirring at room temperature and 6 ml (0.042 moles) of triethyl-amine are added under stirring. During the addition of the triethylamine a temperature elevation of 3°–4° C. may be observed. The reaction mixture is stirred for two hours at 25°–30° C., until a clear solution is obtained. The unreacted starting material (the active ester) is filtered, whereafter the solution is cooled to 0°–2° C. and crystallized. The precipitated crystals are filtered and washed with cold anhydrous alcohol of −5° to 0° C. Yield: 6.7–7.0 g (75–80%) of 2-(1,3-dioxolan-2-yl)-phenyl-N-methyl-carbamate. Mp.: 113°–116° C.

EXAMPLE 2

3.1 g (0.0254 moles) of salicylic aldehyde are dissolved in 30 ml of anhydrous toluene and 8.1 g (0.025 moles) of N-methyl-carbamic acid-pentachlorophenyl-ester are added under stirring at room temperature, whereafter 2.6 g (0.0257 moles) of triethylamine are added to the mixture under stirring. During the addition of the triethylamine an elevation of the temperature of about 2°–5° C. may be observed. The reaction mixture is stirred at 25°–30° C. for 2 hours, after about 1 hour the reaction mixture becomes clear. The unreacted active ester is filtered, the toluene is removed from the filtrate and the residual oily substance is recrystallized from a three-fold amount of diisopropylether. 2-methyl-carbamoyloxy-benzaldehyde is obtained. Mp.: 128°–132° C.

EXAMPLE 3

6.43 g (0.05 moles) of o-chloro-phenol are dissolved in 40 ml of anhydrous toluene at room temperature and 16.1 g (0.0497 moles) of N-methyl-carbamic acid-pentachlorophenyl-ester are added at room temperature under stirring, whereafter 5.05 g (0.05 moles) of triethylamine are added to the suspension under stirring at 20°–25° C. The reaction mixture is stirred for 2 hours at 25°–30° C., the unreacted ester is filtered, the reaction mixture is cooled to 0°–2° C. and crystallized. The precipitated crystals are filtered and washed with cold anhydrous toluene. The product obtained is 2-chloro-phenyl-N-methyl-carbamate. Mp.: 90°–94° C.

What we claim is:

1. A process for the preparation of a substituted-phenyl-N-alkyl-carbamate of the formula:

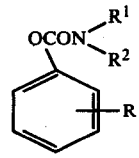

wherein
R$^1$ and R$^2$ are identical or different and each is hydrogen or lower alkyl;
R is halogen, formyl or a group of the formula:

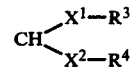

in an ortho or meta position to the carbamaoyloxy group, wherein X$^1$ and X$^2$ are identical or different and each is oxygen or sulfur; and
R$^3$ and R$^4$ are identical or different and each is alkyl, alkenyl, alkynyl, or together for a 5-membered saturated or unsaturated heterocycle in which X$^1$ and X$^2$ are heteroatoms; said process comprising: reacting a compound of the formula:

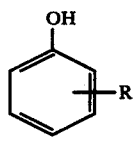

in the presence of a base with a compound of the formula

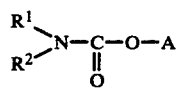

wherein A is pentachlorophenyl.

2. The process defined in claim 1, which comprises carrying out the reaction in an organic solvent selected from the group which consists of toluene, acetone, dioxane and chloroform.

3. The process defined in claim 1 wherein said base is triethylamine.

* * * * *